United States Patent [19]

Bolessa et al.

[11] Patent Number: 5,543,431
[45] Date of Patent: Aug. 6, 1996

[54] ANTI-FUNGAL AGENTS

[75] Inventors: Evon A. Bolessa, Edison; Robert E. Schwartz, Scotch Plains; Gerald F. Bills, Clark; Robert A. Giacobbe, Lavalette, all of N.J.; Fernando Pelaez Perez, Madrid, Spain; Angeles Cabello Arroyo, Madrid, Spain; Teresa Diez Matas, Madrid, Spain; Isabel Martin Fernandez, Madrid, Spain; Francisca Vicente Perez, Madrid, Spain; Suzanne M. Mandala, Scotch Plains, N.J.; Deborah L. Zink, Manalapan, N.J.; Rosemary Thornton, Cranford, N.J.; John R. Thompson, Scotch Plains, N.J.; James E. Curotto, Morgan, N.J.

[73] Assignee: Merck & Co., Inc., Rahway, N.J.

[21] Appl. No.: 449,622

[22] Filed: May 24, 1995

Related U.S. Application Data

[62] Division of Ser. No. 326,986, Oct. 21, 1994.

[51] Int. Cl.$^6$ ............... C07C 233/09; C07C 233/20; A61K 31/695; A61K 31/16
[52] U.S. Cl. ............... 514/627; 514/63; 554/39; 554/63; 554/66
[58] Field of Search ............... 554/63, 66, 39; 514/627, 63

[56] References Cited

PUBLICATIONS

C.A.; 95: 11722t, (1981), vol. 95, Yasuda, et al.
C.A.; 100: 138836s, (1984), vol. 100, Tsuboi, et al.
C.A.; 102: 59229j, (1985), vol. 102, Greger, et al.
C.A.; 113: 12110a, (1990), vol. 113, Tanaka, et al.
C.A.; 115: 71963v, (1991), vol. 115, Bari, et al.
C.A.; 119: 266517t, (1993), vol. 119, Kikuzaki, et al.

*Primary Examiner*—Joseph Paul Brust
*Attorney, Agent, or Firm*—Richard C. Billups; Mark R. Daniel

[57] ABSTRACT

A compound having the formula

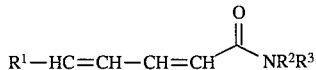

which is an anti-fungal agent is described. The producing organism *Colletotricum accutatum* is also described, along with a method of production.

9 Claims, 5 Drawing Sheets

ANTI-FUNGAL AGENTS

CROSS REFERENCE TO RELATED APPLICATIONS

This application is a divisional application of U.S. application Ser. No. 08/326,986, filed on Oct. 21, 1994, copending herewith, priority of which is claimed hereunder.

BACKGROUND OF THE INVENTION

The present invention relates to anti-fungal compounds, compositions and methods of use. Antifungal compounds presently in use include amphotericin B, ketoconazole, fluconazole and similar agents. These compounds demonstrate varying levels of toxicity, amphotericin B being considered the most toxic. Also, clinical efficacy with these prior antifungal agents has been somewhat lower than desired, particularly in immunocompromised hosts. The present compounds thus provide a valuble alternative treatment for patients with fungal infections.

SUMMARY OF THE INVENTION

The present invention is directed to a compound represented by the formula I:

$$R^1-HC=CH-CH=CH-C(O)-NR^2R^3 \quad\quad I$$

or a pharmaceutically acceptable solvate thereof.

$R^1$ represents a $C_5$ to $C_{15}$ straight or branched chain alkyl group;

one of $R^2$ and $R^3$ represents H and the other is a straight or branched $C_3$ to $C_6$ alkyl group substituted with 1–4 hydroxyl or -OP groups, wherein P represents a hydroxyl protecting group;

or $R^2$ and $R^3$ are joined together and represent a $C_3$ to $C_5$ alkylidene group which forms a ring with the N to which they are attached, said alkylidene group being substituted with 1–4 hydroxyl or -OP groups, wherein P represents a hydroxyl protecting group.

BRIEF DESCRIPTION OF THE DRAWINGS

The invention is described in detail in connection with the drawing attached hereto, in which.

DETAILED DESCRIPTION

The compounds of formula I have antifungal properties, rendering the compounds useful as antifungal agents.

A subset of the compounds described herein is comprised of compounds wherein $R^2$ and $R^3$ are joined together and represent a $C_3$ to $C_5$ alkylidene group which forms a ring with the N to which they are attached. The alkylidene group is substituted with 1–4 hydroxyl or -OP groups, wherein P represents a hydroxyl protecting group.

Illustrative of these compounds is a preferred subset of compounds of formula I wherein $R^2$ and $R^3$ are joined together and represent a $C_3$ to $C_5$ alkylidene group which forms a ring with the N to which they are attached, substituted with 3 groups selected hydroxyl and -OP, wherein P represents a hydroxyl protecting group.

Within this preferred subset of compounds, the alkylidene group can be substituted with 2 hydroxyl groups and one -OP group wherein P is a hydroxyl protecting group.

Illustrative of this preferred subset of compounds, P represents acetyl, $CH_3C(O)$.

One particular sub-type of compounds which falls within this preferred subset of compounds is the following:

$$R^1-HC=CH-CH=CH-C(O)-N\text{(ring with }OC(O)CH_3, OH, OH\text{)} \quad\quad \text{I-a}$$

wherein $R^1$ is as previously defined.

Another subset of compounds of formula I is comprised of compounds wherein $R^1$ represents a branched $C_{5-15}$ alkyl group. Preferably, the $R^1$ group of these compounds is a $C_{10}$ branched alkyl group. An example of this subset of compounds is of the formula:

$$CH_3(CH_2)_7CH(CH_3)-HC=CH-CH=CH-C(O)-NR^2R^3 \quad\quad \text{I-b}$$

wherein $R^2$ and $R^3$ are as previously defined.

Preferred species of the invention include the following compounds:

I-c: [structure with long alkyl chain, diene, amide, ring with OH, OC(O)CH₃, OH]

I-d: [structure with long alkyl chain, diene, amide, ring with OH, OH, OH]

-continued

[Structure I-e: long alkyl chain with C=C, C(O)NH linked to pyrrolidine ring bearing OH, OH, OC(O)CH₃]

[Structure I-f: long alkyl chain with C=C, C(O)NH-CH₂-CH(OH)-CH(OH)-CH₂OH]

[Structure I-g: long alkyl chain with C=C, C(O)NH-CH₂-CH₂-CH(OH)-CH₂OH]

[Structure I-h: long alkyl chain with C=C, C(O)NH-CH₂-CH(OC(O)CH₃)-CH(OH)-CH₂OH]

[Structure I-i: long alkyl chain with C=C, C(O)NH-CH₂-CH(OH)-CH(OH)-CH₂-OC(O)CH₃]

[Structure I-j: long alkyl chain with C=C, C(O)NH-CH₂-CH(OC(O)CH₃)-CH(OH)-CH₂OH (variant)]

and

[Structure I-k: long alkyl chain with C=C, C(O)NH-CH₂-CH(OC(O)CH₃)-CH(OC(O)CH₃)-CH₂-OC(O)CH₃]

Many of the compounds of formula I are conveniently produced by cultivating a species of *Colletothricum accutatum*, maintained as 9225-301F in the culture collection of Merck & Co., Rahway, N.J. and which has been deposited under the Budapest Treaty in the Culture Collection of the American Type Culture Collection at 12301 Parklawn Drive, Rockville, Md., 20852 and assigned accession number 74288, deposited on Jul. 6, 1994 pursuant to the Budapest Treaty. The organism constitutes another aspect of the present invention.

During preparation, the isolate was grown on sterilized banana leaves in order to see its normal morphology and was identified as *C. acutatum*. This species is widely distributed, with most reports emanating from warmer regions of New Zealand, Australia, Asia, Africa and North America.

*Colletotrichum acutatam* Simmonds (MF5866)

Isolated from flowers of unknown Moraceae, Reserva Biológica Bosque Nubosa Monteverde, Guanacaste Province, Costa Rica.

Colonies growing moderately fast on oatmeal agar (Difco Laboratories). 25° C., 12 hr photoperiod, after 10 days attaining 34–35 mm in diameter, slightly raised, zonate, with abundant pale orange (Salmon Color, Light Ochraceous Salmon, Pinkish Cinnamon) conidiomata (capitalized color names from Ridgway, R. 1912. Color Standards and Nomenclature, Washington, D.C.), with dark gray microsclerotia forming in old regions of colony, with aerial mycelium floccose to cottony, with white to pale gray to gray (Pearl Gray, Dawn Gray, Light Olive Gray, Hathi Gray), margin white, even. Reverse dull olivaceous gray (Olive Gray). Exudates and odors absent.

Colonies growing moderately fast on YM agar (Difco Laboratories). 25° C., 12 hr photoperiod, after 10 days attaining 38 mm in diameter, raised, zonate, felty to cottony, dark gray (Hathi Gray, Deep Olive Gray) towards center, otherwise white, with scattered pale orange conidiomata, margin even, submerged. Reverse creamy yellow, mottled with gray. Exudates and odors absent.

No growth on YM agar at 37° C.

Colonies growing moderately fast on V8 juice agar (Mycology Guidebook, University of Washington Press, p. 665, medium M-29). 25° C., 12 hr photoperiod, after 10 days attaining 38–40 mm in diameter, slightly raised, zonate, floccose to cottony, white to pale gray in age, margin even submerged. Reverse creamy yellow, mottled with gray. Exudates and odors absent.

Conidiomata grown on surface of autoclaved banana (Mus paradisica) leaves acervuli, pulvinate, superficial or shallowly embedded in cuticle, up to 1.5 m in diameter, gregarious, usually coalescing in age, occasionally intermingled with microsclerotia, with a thin basal stromata composed of a textura angularis, exuding moist, slimy masses of conidia; conidial masses dull grayish pink to salmon-colored when moist, yellowish orange to cream-colored upon desiccation. Conidiogenous cells enteroblastic, phialidic, arising directly from upper cells of stromata of conidiomata, arranged in a dense palisade on surface of stromata, usually branched 2–3 times at point of origin, occasionally with a single branch at higher levels, 15–29× 3–4 µm, tapered upward, straight to slightly curved or flexuous, thin-walled, terminating in a narrow pore surrounded by periclinal thickenings, often with a slight fringe of slightly flared collarette surrounding the conidiogenous locus. *Conidia ellipsoidal,* slightly to distinctly attenuated at distal end, with proximal end attenuated, truncate, 11–15.5× 3–4 µm, smooth, thin-walled, hyaline, often biguttulate. Setae not observed on leaves or on agar. No teleomorph observed.

This fungus is assigned the anamorph genus Colletotrichum because the conidiomata are open acervuli, the conidiogenous cells are supported by a thin basal stroma, the conidiogenous cells are phialides, and the conidia are ellipsoidal, hyaline, accumulating in slimy orange masses. Using the diagnostic guide provided by Baxter et al. (A. P. Baxter, G. C. A. van der Westhizen & A. Eicker. 1983. Morphology and taxonomy of South African isolates of Colletotrichum. South African Journal of Botany 2:259–289), the isolate is best identified as *C. acutatum* based on the relatively small conidia which are ellipsoidal with attenuated ends, absence of setae, and gray colony colors. According to B. J. Dyko and J. E. M. Mordue (1979 Commonwealth Mycological Descriptions of Pathogenic Fungi and Bacteria No. 630), some isolates of *C. acutatum* may produce microsclerotia or sclerotia as were observed in MF5866. To best of our knowledge this would be the first recorded occurrence of *C. acutatum* in Costa Rica (Covington, D. J. 1980. Fungi Costaricensis: A checklist of reported species. Tulane University. M.S. thesis).

FERMENTATION CONDITIONS

In general the compounds of structural formula I can be produced by culturing (fermenting) the above described strain, Merck number MF6037 (ATCC 74288) in a solid millet-based fermentation medium containing assimilable carbon and nitrogen sources, preferably under static aerobic conditions, under constant fluorescent light until a substantial amount of compounds of structural formula I is detected in the fermentation extract. The culture is incubated in a solid millet-based medium at a temperature between 20° C. and 37° C., preferably 25° C., for a period of time sufficient to generate compounds of structural formula I, usually from about 3 to about 28 days, preferably about 3 to about 7 days. In addition, the above described strain can be incubated under submerged aerobic conditions with shaking on a rotary shaker, operating at 220 rpm with a 5 cm throw with all other physical incubation parameters remaining the same as for the solid-based medium. The aqueous production medium is maintained at a pH between about 5 and 8, preferably about 6.0 to 6.2, at the initiation and termination (harvest) of the fermentation process. The desired pH may be maintained by the use of a buffer, such as [2-(N-morpholino)ethanesulfonic acid]monohydrate (MES), 3-(N-morpholino)propanesulfonic acid (MOPS), phosphate buffer and the like, or by choice of nutrient materials which inherently possess buffering properties, such as production media described herein below. Extracting the active compound from the mycelial growth of the culture is preferably done with methanol (MeOH) or with a suitable solvent, concentrating the solution containing the desired compound, then subjecting the concentrated material to chromatographic separation to isolate the compound or compounds from the cultivation medium.

The preferred sources of carbon in the nutrient medium include maltose, mannitol, glucose, sucrose, glycerol, xylose, galactose, fructose, lactose, sorbitol, starch, dextrin, other sugars and sugar alcohols, starches and other carbohydrates, or carbohydrates derivatives, and the like. Other sources which may be included are rhamnose, raffinose, arabinose, mannose and the like, as well as complex nutrients such as brown millet, rice, oat flour, yellow corn meal, rice, cracked corn, and the like. The exact quantity of the carbon source which is utilized in the medium will depend, in pan, upon the other ingredients in the medium, but it is usually found that an amount of carbohydrate between 0.5 and 15 percent by weight relative to the weight of the medium is satisfactory. These carbon sources can be used individually or several such carbon sources may be combined in the same medium.

The preferred sources of nitrogen are yeast extract, NZ Amine type E, yellow corn meal, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids such as methionine, phenylalanine, serine, alanine, proline, glycine, arginine or threonine, and the like. The various sources of nitrogen can be used alone or in combination in amounts ranging from 0.2 to 10 percent by weight of the medium.

The carbon and nitrogen sources, though advantageously employed in combination, need not be used in their pure form. Less pure materials which contain traces of growth factors and considerable quantities of mineral nutrients are also suitable for use. When desired, there may be added to the medium inorganic salts, sodium, potassium, magnesium, calcium, phosphate, sulfate, chloride, carbonate, and like ions which can be incorporated in the culture medium as sodium or calcium carbonate, sodium or potassium phosphate, sodium or potassium chloride, sodium or potassium iodide, magnesium salts, copper salts, cobalt salts, and the like. Also included are trace metals such as cobalt, manganese, iron, molybdenum, zinc, cadmium, copper, and the like. The various sources of inorganic salts can be used alone or in combination in amounts ranging from 0.1 to 1.0 percent, and trace elements ranging from 0.001 to 0.1 percent by weight relative to the weight of the medium.

In addition, production of these compounds also occurs under submerged aerobic conditions by shaking the culture at 220 rpm on a rotary shaker with a 5 cm throw. When the growth is carried out in large tanks, it is preferable to use the vegetative form of the organism for inoculation in the production tanks in order to avoid growth lag in the process of producing a compound of structural formula I. Accordingly, it is desirable to initially produce a vegetative inoculum of the organism by inoculating a relatively small quantity of culture medium with spores or mycelia of the organism, and culturing said inoculated medium, also called the "seed medium", and then to transfer the cultured vegetative inoculum aseptically to large tanks. The seed medium, in which the inoculum is produced may be seen in Table 1, and is generally autoclaved to sterilize the medium prior to inoculation. The seed medium is generally adjusted to a pH between about 5 and 8, preferably about 6.8, prior to the autoclaving step by the addition of a suitable acid or base, preferably in the form of a buffering solution. Growth of the culture in this seed medium is maintained between about 20° C. and 37° C., preferably 250° C. Incubation of culture MF6037 in seed medium (Table 1) is usually conducted for a period of about 2 to 6 days, preferably 3 to 4 days, on a rotary shaker operating at 220 rpm with a 5 cm throw. The length of incubation time may be varied according to fermentation conditions and scales.

If appropriate, a second stage seed fermentation may be carried out in the seed medium for greater production of mycelial mass by inoculating fresh seed medium with a portion of the culture growth and then incubating under similar conditions but for a shortened period. The resulting growth may then be employed to inoculate the production medium 1, 2 or 3 (Tables 2, 3 and 4).

The fermentation production medium 2 or 3 inoculated with the seed culture growth is incubated for about 3 to 28 days, usually 3 to 14 days, with agitation. Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

A preferred fermentation process for the production of the compounds of formula I by Colletotrichum sp. is as follows: Vegetative mycelia of the culture were prepared by inoculating seed medium (Table 1) with mycelia in 10% glycerol. Seed cultures were incubated for 3 days at 25° C. and 50% relative humidity with constant fluorescent light. Two-ml portions of the culture were then used to inoculate a second stage seed culture and further incubated for 3 days as stated above. Two-ml portions of this 3 day culture were used to inoculate a solid millet-based production medium 1 (Table 2) or 50 mL portions of liquid production media 2 or 3 (Tables 3 and 4). The liquid fermentation flasks were shaken and the solid millet-based medium was grown under static conditions. All other incubation parameters remained the same as stated above.

Maximal production of the compounds of formula I occured in the solid millet-based production medium 1 at day 4 (30–40 mg/L). In liquid production medium 3, maximal production occured between 7–14 days (50 mg/L).

TABLE 1

SEED MEDIUM

| | per liter | Trace Element Mix | per liter |
|---|---|---|---|
| Corn Steep Liquor | 5 g | $FeSO_4.7H_2O$ | 1 g |
| Tomato Paste | 40 g | $MnSO_4.4H_2O$ | 1 g |
| Oat flour | 10 g | $CuCl_2.2H_2O$ | 25 mg |
| Glucose | 10 g | $CaCl_2$ | 100 mg |
| Trace Element Mix | 10 ml | $H_3BO_3$ | 56 mg |
| | | $(NH_4)_6Mo_7O_{24}.4H_2O$ | 19 mg |
| PH = 6.8 | | $ZnSO_4.7H_2O$ | 200 mg |

TABLE 2

PRODUCTION MEDIUM 1

| Component | Amount (per 250-ml flask) |
|---|---|
| Millet | 15 g |
| Yeast Extract | 0.5 g |
| Sucrose | 0.5 g |
| Alfalfa | 0.5 g |

TABLE 2-continued

PRODUCTION MEDIUM 1

| Component | Amount (per 250-ml flask) |
|---|---|
| $FeSO_4.7H_2O$ | 0.01 g |
| Corn Oil | 0.1 ml |
| Sodium Tartrate | 0.1 g |
| Distilled Water | 15 ml |

The pH was not adjusted prior to autoclaving for 20 min. Immediately before use, the medium was moistened with 15 ml of water and autoclaved again for 20 min.

TABLE 3

PRODUCTION MEDIUM 2

| Component | per liter |
|---|---|
| Mannitol | 75 g |
| Oat Flour | 15 g |
| Fidco Yeast Extract | 5 g |
| L-Glutamic Acid | 4 g |
| MES* | 16.2 g |

The pH was adjusted to 6.0 with NaOH before autoclaving.
*2-(N-morpholino)-ethanesulfonic acid

TABLE 4

PRODUCTION MEDIUM 3

| Component | per liter |
|---|---|
| Maltose | 100 g |
| NZ-Amine type E | 33 g |
| Fidco Yeast Extract | 10 g |
| MES* | 16.2 g |

The pH was adjusted to 6.2 with NaOH before autoclaving.
*2-(N-morpholino)-ethanesulfonic acid Many of the hydroxyl groups which are substituted on $R^2$ and $R^3$ are in protected form. Examples of suitable hydroxyl protecting groups are: t-butylmethoxyphenylsilyl, t-butoxydiphenylsilyl, trimethylsilyl (TMS), triethylsilyl (TES), t-butyldimethylsilyl (TBDMS), o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. The hydroxy protecting groups can be added, removed and changed to different groups using standard protection/deprotection techniques. The preferred hydroxyl protecting groups are acetyl and the silyl containing groups.

The compounds of formula I have antifungal activity. The usefulness of the compounds as antifungal agents may be demonstrated in a broth microdilution assay for the determination of minimum inhibitory concentrations (MIC) and minimum fungicidal concentrations (MFC) against fungi. A panel of fungi is selected for resistance/susceptibility to known compounds, animal virulence, source, overall clinical importance and other factors.

In the microbroth dilution assay, microorganisms are selected by streaking a yeast culture on Sabouraud dextrose agar (SDA) and incubating for 24–48 hours at 35°–37° C. Thereafter, 3 to 5 characteristic colonies are selected, transferred to a fresh plate and incubated under similar conditions. From the regrowth, 3 to 5 colonies are selected and suspended in 10 mls of YM broth (Difco) and incubated for 4 hours at 35°–37° C. shaking at 225 rpm. The 4 hour broth cultures are adjusted optically to 86% transmission, resulting in a concentration of 1–5×10⁶ cfu/ml which was further diluted 1:100 in YNBD (yeast nitrogen base with 1% dextrose) to obtain a concentration of 1–5×10⁴ cfu/ml for use as inocula.

Test compounds and control compounds were prepared as stock solutions of 512 mg/ml in 10% DMSO and 75 ml of said solution delivered to each well in column 1 of a 96-well, U-bottomed microtiter plate. The compounds in column 1 were then serially diluted two-fold to yield concentrations from 128 mg/ml to 0.5 mg/ml.

The plates containing the diluted compounds were then inoculated with 75 ml/well of the appropriate microorganism and incubated for 48 hours at 35°–37° C. with MIC determinations carried out after 24 hours of incubation. Growth and sterility controls for each organism and sterility checks for the compounds also were also carded out.

After recording MIC values at 24 hours, the microtiter plates were shaken gently to resuspend the cells. A 1.5 µl sample was transferred from each well of the 96-well microtiter plate to a single reservoir inoculum plate containing SDA. The inoculated SDA and corresponding microtiter plates were incubated for 24 hours at 35°–37° C. For *Cryptococcus neoformans*, SDA plates were inoculated at 48 hours after recording MIC values and incubated 48 hours before reading the MFC values. The MFC is the lowest concentration of compound at which either no growth or growth of ≦4 colonies occur.

Data which exemplifies the anti-fungal activity of the compounds of the present invention is provided below. Such activity in vitro is predictive of utility as an anti-fungal agents when the compounds are administered to a mammalian patient in need of such treatment, in an amount which is effective to treat a fungal infection.

| Strain | I-e | | I-f | |
| --- | --- | --- | --- | --- |
| | MIC24 | MFC | MIC24 | MFC |
| C. albicans (MY1028) | 4 | 4 | 128 | >128 |
| C. albicans (MY1055) | 4 | 4 | >128 | 128 |
| C. albicans (MY1750) | 8 | 8 | >128 | >128 |
| C. guillermondii (MY1019) | 4 | 4 | 128 | >128 |
| C. parapsilosis (MY 1010) | 2 | 0.5 | 64 | 16 |
| C. pseudotropicalis (MY2099) | 1 | 0.5 | 32 | 32 |
| C. tropicalis (MY1012) | 0.25 | 0.25 | | |
| C. neoformans (MY1051) | 2 | 2 | 32 | 32 |
| C. neoformans (MY1146) | 8 | 8 | 64 | 128 |
| C. neoformans (MY2061) | 0.25 | 4 | 64 | 64 |
| C. neoformans (MY2062) | 1 | 2 | 64 | 64 |
| S. cerevisiae (MY1976) | >32 | | | |
| A. flavus (MY0383) | 8 | | >128 | |
| A. fumigatus (MF4839) | 8 | | >128 | |
| A. fumigatus (5668) | 4 | | >128 | |
| A. fumigatus (5669) | 4 | | >128 | |

The pharmaceutical composition of the invention described herein includes a compound of formula I in combination with a pharmaceutically acceptable carrier.

The compound of the invention may be used in a variety of pharmaceutical preparations. Compositions for injection, the preferred route of delivery, may be prepared in unit dosage form in ampoules or in multidose containers. The compositions may take such forms as suspensions, solutions or emulsions, oily or aqueous in nature, and may contain various formulating agents, such as diluents, buffers, preservatives and the like. Hence, the compound is present in combination with these pharmaceutically acceptable carriers.

Alternatively, the compound may be in the form of a sterile powder, which can be reconstituted with a suitable carrier such as sterile water, normal saline and the like at the time of administration. The powder can be in lyophillized or non-lyophillized form.

Oral compositions are typically in the form of tablets, capsules, solutions or suspensions. Such compositions may likewise be packaged in unit dose or multidose containers. In these oral compositions, the pharmaceutically acceptable carriers may be comprised of diluents, tabletting and granulating aids, lubricants, disintegrants, buffers, flavorants, sweeteners, preservatives and the like.

Topical compositions may be comprised of a compound of formula I in combination with a pharmaceutically acceptable carrier, in the form of hydrophobic or hydrophilic ointments, creams, lotions, solutions, paints or powders.

The invention described herein further includes a method of treating a fungal infection in a mammal in need of such treatment, comprising administering to said mammal a compound in accordance with formula I in an amount effective to treat a fungal infection.

The dosage to be administered depends to a large extent upon the condition and size of the subject being treated as well as the route and frequency of administration. The parenteral route (by injection) is preferred for generalized infections. Such matters, however, are typically left to the discretion of the clinician according to principles of treatment well known in the infectious disease arts.

The compositions for human delivery per unit dosage, whether liquid or solid, may contain from about 0.01% to about 99% of active material, the preferred range being from about 1.0–60%. The composition will generally contain from about 1.5 mg to about 2000 mg of the active ingredient; however, in general, it is preferable to employ a dosage amount in the range of from about 25 mg to 1000 mg. In parenteral administration, the unit dosage is usually the compound I in a sterile water or saline solution or in the form of a soluble powder intended for solution.

The preferred method of parenteral administration of the compound of formula I is by intravenous (i.v.) infusion. Alternatively, the compound may be administered intramuscularly (i.m.).

For adults, a dose of about 0.5 to about 50 mg of the formula I compound per kg of body weight is administered from 1 to 6 times per day. The preferred dosage ranges from about 2 mg to 1000 mg of the compound may given one to four times per day.

More specifically, for mild infections a dose of about 2.5–250 mg two to four times daily is preferred. For moderate infections against highly susceptible organisms a dose of about 5–500 mg b.i.d. to q.i.d. is preferred. For severe, life-threatening infections against organisms at the upper limits of sensitivity, a dose of about 10–2000 mg two to six times daily is preferred.

For children, a dose of 0.5–25 mg/kg of body weight given 1 to 4 times per day is preferred; a dose of 1.0-mg/kg b.i.d., t.i.d. or q.i.d. is preferred.

The invention is further illustrated in connection with the following non-limiting examples.

EXAMPLE 1

FERMENTATION OF COLLETOTRICHUM

Fermentation conditions for the production of compounds of formula I by Colletotrichum sp. were as follows: Vegetative mycelia of the culture were prepared by inoculating 54 ml of seed medium (Table 1) in a 250 ml unbaffled Erlenmeyer flask with 2 ml of mycelia in 10% glycerol (MF6037 wt) that had been stored at −80° C. Seed cultures were incubated for 3 days at 25° C. and 50% relative humidity on a rotary shaker with a 5-cm throw at 220 rpm in a room with constant fluorescent light. Two-ml portions of the culture were then used to inoculate a second stage seed culture and further incubated for 3 days as stated above.

Figure 1:
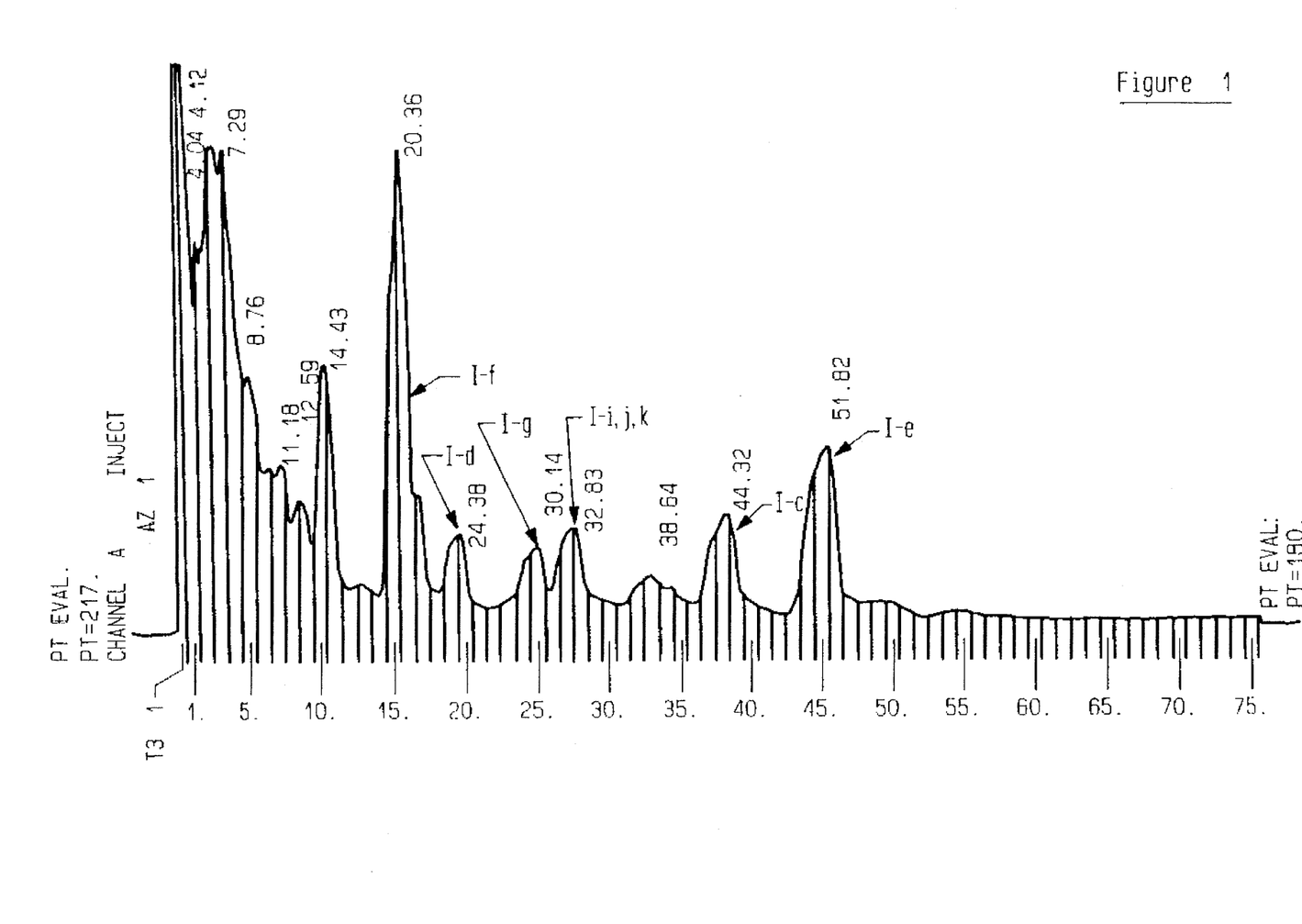
FIG. 1 is an HPLC trace derived in accordance with Example 1.

The fractions eluted with 60% EtOAc/hexane, 100% EtOAc and 10% MeOH/EtOAc were collected. Also, a portion (50%) of the fraction which eluted with 10% MeOH/EtOAc from the SiO$_2$ column was further purified by HPLC using a Zorbax RX C-8 column and eluting with MeOH/H$_2$O (70:30). Active components (Compounds I-c, I-d and I-f through I-j) eluted at 17 minutes as a well resolved peak (5 mg.). An HPLC trace of this fraction is as shown in FIG. I.

Compound I-f was found to have the following spectral characteristics:

Mass spectroscopic data for compound I-f is derived from scanning HREI-MS, indicating a molecular formula of $C_{19}H_{35}NO_4$.

The infrared spectrum showed absorptions at 3317, 1653, and 1551 cm$^{-1}$.

The ultraviolet spectrum exhibited an absorption maximum at ($1_{max}$MeOH) at 264 nm (e 35,055).

Figure 2:
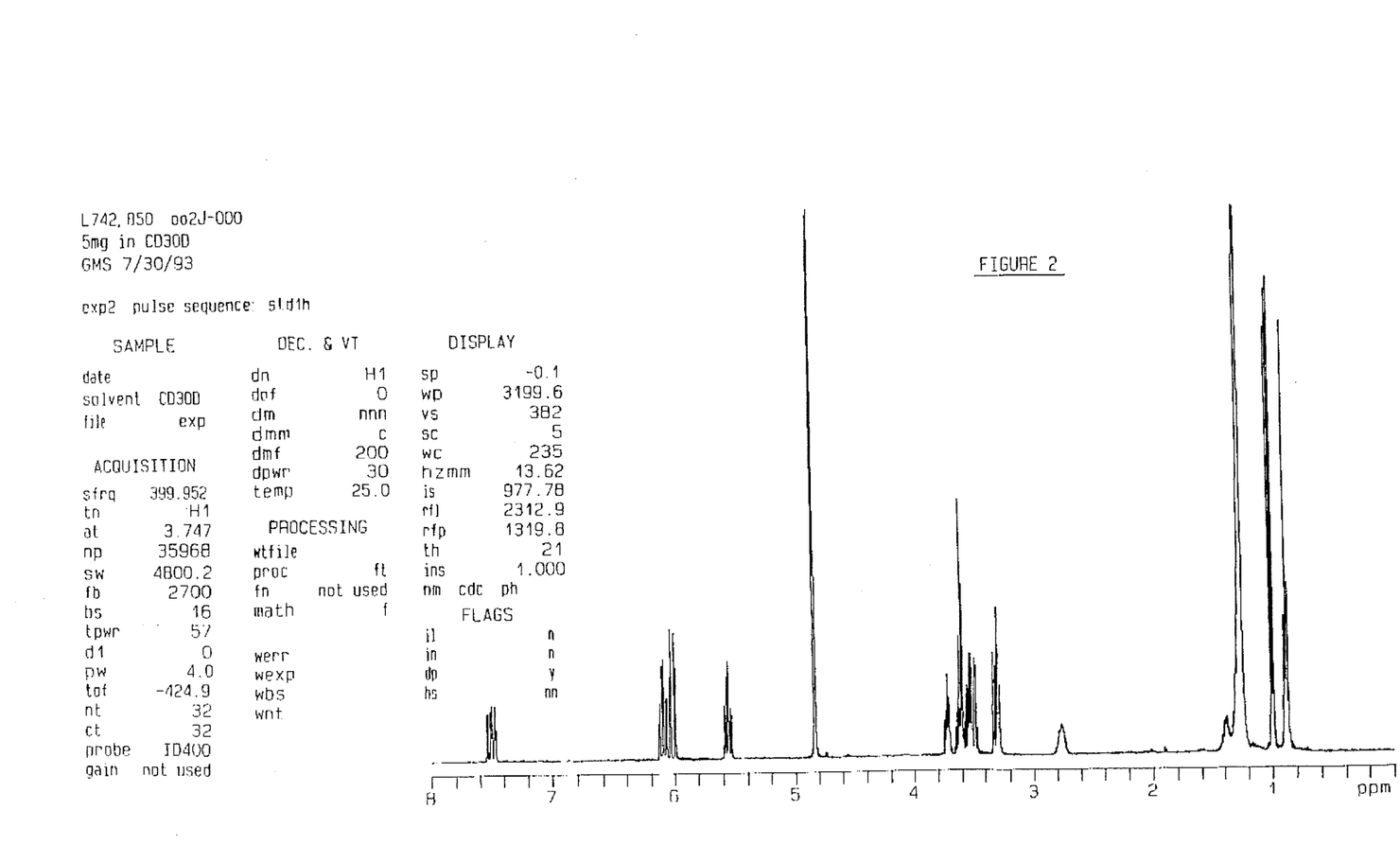
FIG. 2 is an NMR of compound I-f, derived in accordance with Example 1.

The $^1$H chemical shift assignments (NMR) for compound I-f are shown in FIG. 2.

Two-ml portions of this 3 day culture were used to inoculate a solid millet-based medium 1 (Table 2) or 50 ml portions of liquid production media 2 or 3 (Tables 3 and 4) in 250 ml unbaffled Erlenmeyer flasks.

The liquid fermentation flasks were shaken at 220 rpm and the solid millet-based medium was grown under static conditions. All other incubation physical parameters remained the same as stated above.

Maximal production of compounds I-e and I-c in solid millet-based medium 1 occured by day 4 (30–40 mg/L). In liquid medium 3, maximal production of compound I-e occured between 7–14 days (50 mg/L). At harvest, compound I-c and compound I-e were extracted from the cell pellet with equal volumes of either methanol or acetonitrile (liquid media), or with 50 mL per 250 mL Erlenmeyer flask from the solid millet-based medium 1 by shaking with the solvent at 220 rpm for 1 hour at 25° C. The samples were centrifuged for 20 minutes at 3000 rpm to obtain clear extract.

ISOLATION

The MeOH extract (3 L) of a solid fermentation of Colletothricum sp. was diluted (to 15 L with H$_2$O) and adsorbed on a 1 liter SP-207 column. The MeOH eluate (2 L) was concentrated to 150 mL, half of which was partitioned with hexane (2×70 ml). The MeOH layer from the partition was diluted with water (100 ml) and freeze dried. The freeze dried material (1.8 g) was resuspended in MeOH and the undissolved solids were filtered off.

A slurry of the methanolic solution (1.5 g of the residue in 5 ml) and silica gel (2 ml) was concentrated to dryness and the residue was added to the top of a silica gel column (40 mL), previously equilibrated in hexane. The column was eluted with a gradient of EtOAc/hexane (30:70–100:0) followed by MeOH/EtOAc (1:99–10:90) and finally washed with 15 % MeOH.

Isolation of I-e

Figure 3:
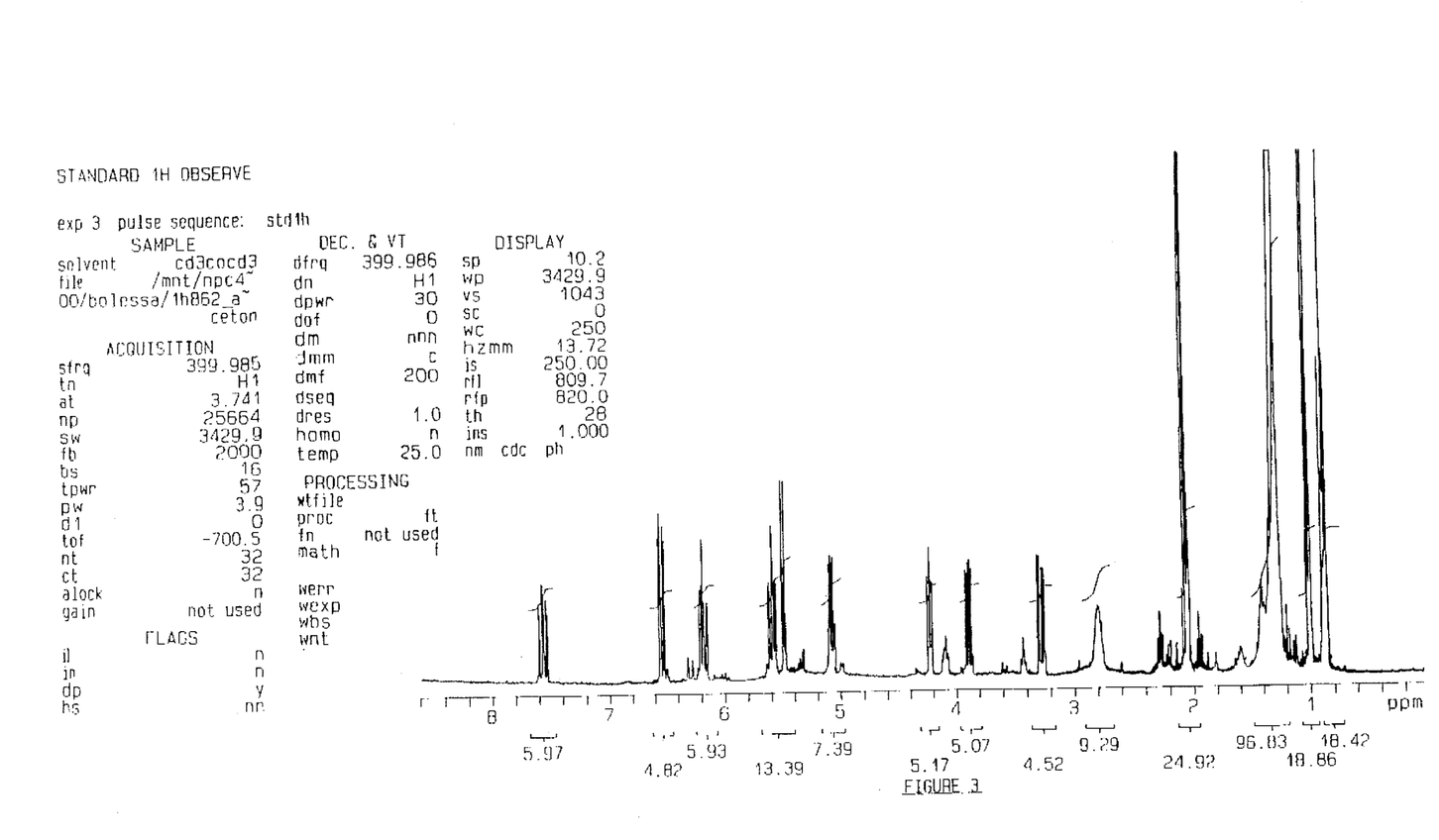
FIG. 3 is an NMR of compound I-e, derived in accordance with Example 1.

An acetonitrile (MeCN) extract of the solid fermentation of C. accutatum was chilled, and the MeCN layer was separated and diluted with CH$_2$Cl$_2$. The resulting water layer separated. The resulting CH$_2$Cl$_2$/MeCN layer was further dried by adding solid NaCl. The dry CH$_2$Cl$_2$/MeCN layer was evaporated to dryness, reconstituted in a mobile phase (MeCN/H$_2$O 1:1) and then loaded onto an open reverse phase column. The column was eluted with MeCN/H$_2$O (1:1) and the fractions containing compound I-e were pooled and diluted with CH$_2$Cl$_2$ (2x volume of the composite). The MeCN/CH$_2$Cl$_2$ solution was evaporated to dryness, reconstituted in MeCN/H$_2$O (1:1) and then fractionated on HPLC eluting with MeCN/H$_2$O (1:1) giving an overall yield of 43%. The NMR for compound I-e is shown in FIG. 3.

Isolation of I-g

Figure 4:
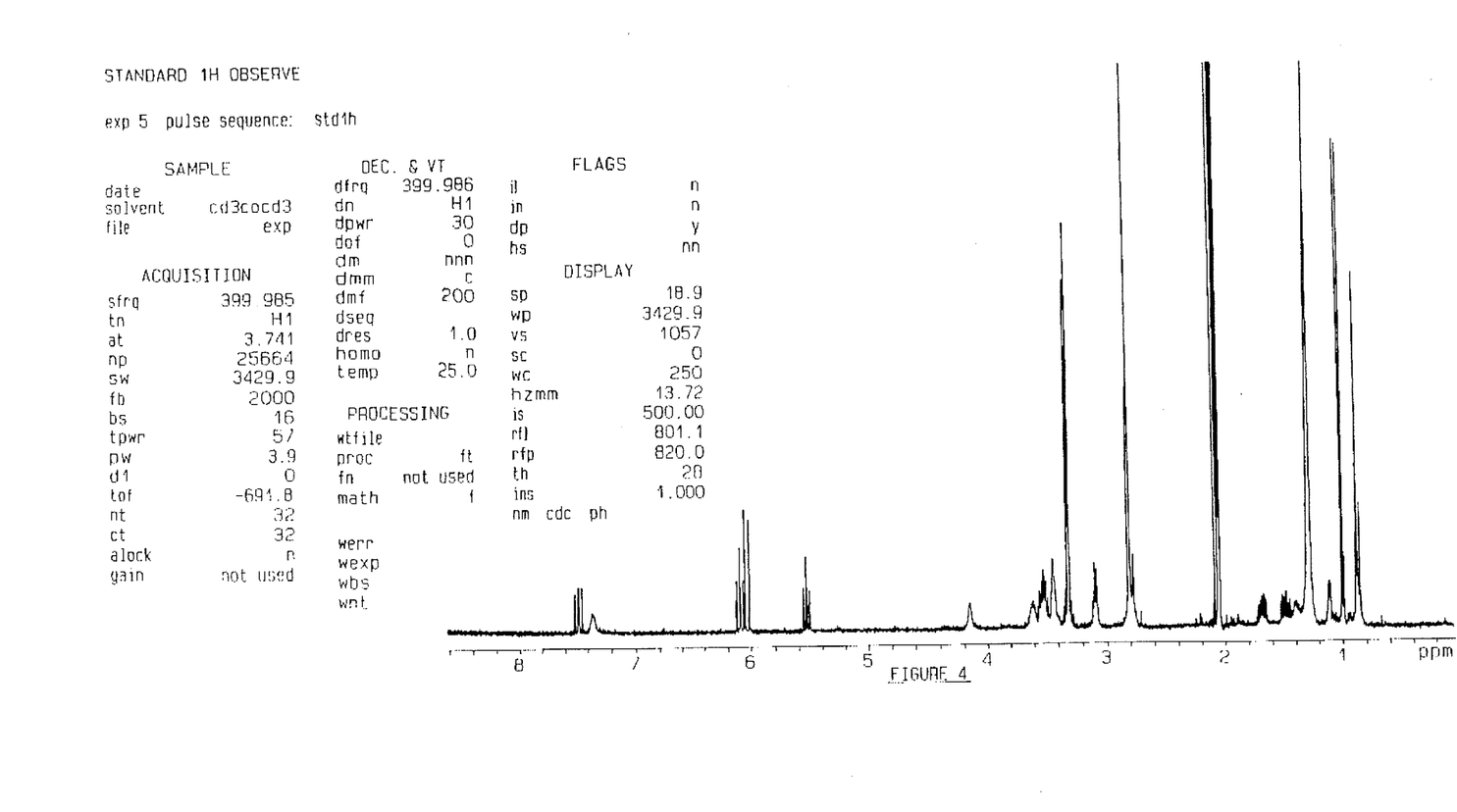
FIG. 4 is an NMR of compound I-g, derived in accordance with Example 1.

The isolation procedure set forth above was repeated, and compound I-g is isolated using reverse phase chromatography. The NMR for compound I-g is shown in FIG. 4.

EXAMPLE 2

A. Synthesis of 1,3-dioxolane

To the triphenylphosphonium salt B (11 mmol) and potassium t-butoxide (11 mmol) in dichloromethane (50 ml) is added the aldehyde A (10 mmol) and 18-crown-6 (30 mg), forming an orange mixture. (Throughout the examples, $R^1$ represents a $C_5$–$C_{15}$ straight or branched chain alkyl group). The mixture is allowed to stir for 1–2 hrs, after which the solvent is removed by evaporation. The residue is washed with petroleum ether and the combined ether washings are filtered through silica gel. Evaporation of the solvent and purification by column chromatography provide predominantly the cis-alkene 1.

B. Synthesis of 2,4-dienoate

A solution of 1 (11 mmol) in THF (50 mL) is stirred at RT. Aqueous HCl (20 ml, 0.2M) is added over 20 minutes with continued stirring for 2 hrs. The solution is reduced in volume to 25 ml and extracted with dichloromethane (3×20 ml). The extract is dried over $MgSO_4$. The deprotected cis-alkene aldehyde C (5.0 mmol) is dissolved in dichloromethane (30 ml) and to this solution is added carbethoxymethylene triphenylphosphorane D (5.1 mmol). The solution is stirred at RT for 12 hrs, while monitoring by TLC. The reaction mixture is then concentrated to dryness, and the residue purified on silica gel, eluting with EtOAc/hexane to provide the dienoate 2.

C. Synthesis of TBDMS (–)-2,3-O-Isopropylidene-D-threitol

To a solution of (–)-2,3-O-Isopropylidene-D-threitol 5 (1.5 mmol) in dry DMF (5.0 ml) is added slowly, at RT, tert-butyldimethylsilyl chloride (TBDMSCl) (1.6 mmol), followed by imidazole (3.5 mmol) with stirring. The reaction mixture is stirred at RT for 18 hrs, while monitoring by TLC. The reaction is quenched by adding saturated NaCl solution (12 ml) and the organic layer is separated. The aqueous layer is extracted with $Et_2O$ (3×50 ml), and the extract is combined with the separated organic layer. The combined organic layers are washed with ice cold 5% HCl and saturated NaCl solution, dried over $MgSO_4$, filtered and concentrated. The residue is purified by column chromatography eluting with EtOAc/hexane.

The monosilyl derivative of (–)-2,3-O-isopropylidene-D-threitol 5 (2.0 mmol), $ZnN_6.2Py$ (1.5 mmol) and triphenyl phosphine ($Ph_3P$) (4.0 mmol) are suspended in dry toluene (10 ml). To this stirred suspension at RT is slowly added diethyl azodicarboxylate (DEAD, 4.0 mmol). The reaction is monitored by TLC and after about 2 hrs, the mixture is filtered through celite, concentrated in vacuo and purified by column chromatography (silica gel, 70–230 mesh) eluting with EtOAc/hexane.

D. Synthesis of Compound 3

The TBDMS azide 6 (2.0 mmol) is dissolved in MeOH and hydrogenated over Raney nickel to provide amine 3.

E. Synthesis of Compound 4

15
-continued

AlMe$_3$ (1.0 mmol of 2M hexane solution) is slowly added to a solution of the amine 3 (1.0 mmol) in CH$_2$Cl$_2$ (5.0 ml) at RT. Stirring is continued for 15 minutes, after which ester 2 is added slowly in CH$_2$Cl$_2$ (5.0 ml). Stirring is continued for another hour at RT and then the reaction mixture is carefully acidified to pH 4 with 1M HCl and stirred for an additional hour.

The aqueous layer is extracted with CH$_2$Cl$_2$ and the combined organic layer is dried over MgSO$_4$ and purified by column chromatography eluting with EtOAc/hexane to provide 4.

F. Silyl Group Deprotection

To a solution of compound 4 (0.5 mmol) in THF is added tetrabutylammonium fluoride (1.5 mmol of 1M in THF) and acetic acid (1.5 mmol) and the solution is stirred at RT for 24 hrs. The reaction mixture is then concentrated in vacuo and added to water. The aqueous solution is extracted with Et$_2$O (3×50 ml), and the extract dried over MgSO$_4$. The dried extract is then purified by column chromatography eluting with EtOAc/MeOH to produce 7.

G. Peracetylation

Figure 5:
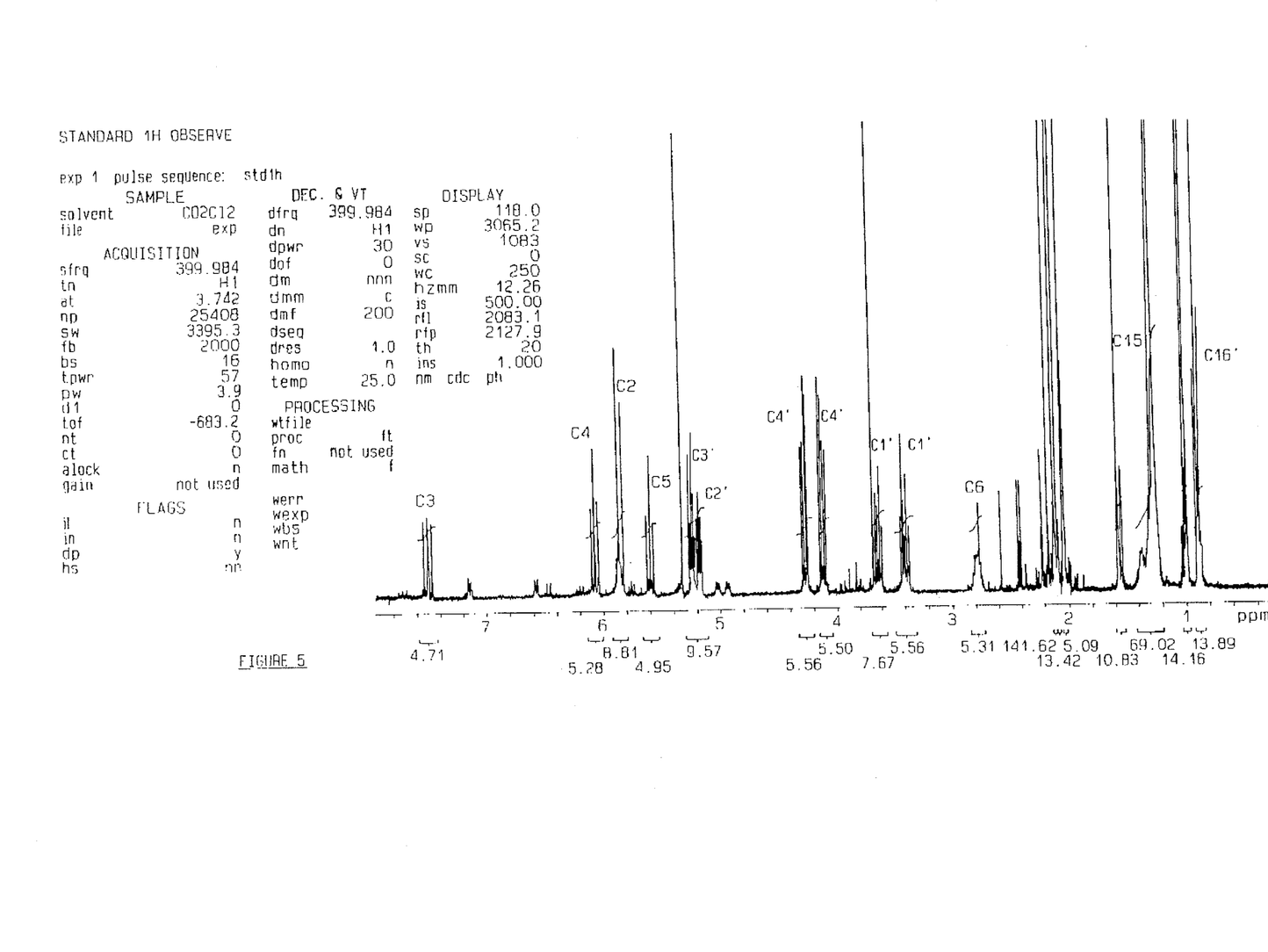
FIG. 5 is an NMR of compound I-k, derived in accordance with Example 3.

Compound 7 from part F above is peracetylated by combining 7 with 4 equivalents (excess) acetyl chloride or acetic anhydride in dichloromethane, in the presence of Et$_3$N. The NMR for compound I-e is shown in FIG. 5.

16
EXAMPLE 3

Monoacetyl dienamide 8 can be obtained by fermentation and separation or synthetically as in Example 2, part F above.

To a solution of 8 (1.0 mmol) dissolved in THF (5.0 ml) is added 5% NaCO$_3$ (20 ml) with stirring at RT. The reaction is stirred for 12 hrs at RT while monitoring by TLC. The reaction mixture is carefully acidified to pH 7 with 1M HCl, extracted with CH$_2$Cl$_2$ and the organic layer dried with MgSO$_4$ producing 7 in deprotected form.

Compound 8 (1.0 mmol) dissolved in CH$_2$Cl$_2$ (10 ml), imidazole (2.0 mmol) and the protecting compound P-X (1.2 mmol,) are allowed to react under nitrogen. The crude protected product is purified by chromatography to produce 9.

The acetyl compounds shown below can be reacted in accordance with Example 3 to provide the compound in column 4.

| X | P | −OP Position |
|---|---|---|
| 2' | Cl | TMS | 2' |
| 3' | Cl | TES | 3' |
| 4' | Cl | benzyl | 4' |
| 2' | Cl | benzhydryl | 2' |
| 3' | Cl | TBDMS | 3' |
| 4' | Br | TMS | 4' |
| 2' | Br | TES | 2' |

| | | | |
|---|---|---|---|
| 3' | Br | benzyl | 3' |
| 4' | Br | TBDMS | 4' |

EXAMPLE 4

EXAMPLE 5

Compound 15 can be synthesized in accordance with the reaction scheme provided above. A protected pyrroline 10 undergoes a Sharpless dihydroxylation, using osmium tetroxide (Admix A or B, Aldrich Chemicals, Inc.). The resulting dihydroxy pyrroline 11 can be protected, using 2,2-dimethoxypropane and a catalytic amount of p-toluene sulfonic acid (PTSA) to produce acetonide 12. Acetonide 12 in turn is N-deprotected by combining with tetrabutylammonium fluoride to produce the nitrogen deprotected acetonide 13. Acetonide 13 is then reacted with the ethyl ester 2 in accordance with Example 2, Part E. The acetonide 14 is thereafter deprotected by treatment with aqueous acid (HCl) to produce compound 15.

Following the procedure set forth in Example 4, and substituting the appropriately substituted pyrrolidone 10a for pyrroline 10, the trihydroxypyrrolidinyl compound I-d can be produced.

EXAMPLE 6

1000 hard gelatin capsules, each containing 500 milligrams of Compound I are prepared from the following formulation:

| Compound | Grams |
|---|---|
| Compound I | 500 |
| Starch | 750 |
| Dibasic calcium phosphate hydrous | 5000 |
| Calcium stearate | 2.5 |

The finely powered ingredients are mixed well and granulated with 10 percent starch paste. The granulation is dried and compressed into tablets.

EXAMPLE 7

1000 hard gelatin capsules, each containing 500 milligrams of Compound I are prepared from the following formulation:

| Compound | Grams |
|---|---|
| Compound I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE 8

250 milliliters of an injectable suspension are prepared by conventional procedures having the following formulation:

| 5% DMSO/water | 250 milliliters |
|---|---|
| Compound I | 400 milligrams |

EXAMPLE 9

An ointment suitable for topical application may be prepared by intimately dispersing 13 milligrams of Compound I in 1 gram of commercially available polyethylene/hydrocarbon gel.

EXAMPLE 10

An aerosol composition may be prepared having the following formulation:

|  | Per Canister |
|---|---|
| Compound I | 24 mg |
| Lecithin NF, liquid concentrate | 1.2 mg |
| Trichlorofluoromethane | 4.025 g |
| Dichlorodefluoromethane | 12.15 g |

While the preferred embodiments of the invention have been described herein in detail, numerous alternative embodiments are contemplated as falling within the scope of the claims.

What is claimed is:

1. A compound represented by the formula:

or a pharmaceutically acceptable salt or solvate thereof, wherein:

$R^1$ represents a $C_5$ to $C_{15}$ straight or branched chain alkyl group;

one of $R^2$ and $R^3$ represents H and the other is a straight or branched $C_3$ to $C_6$ alkyl group substituted with 2–4 hydroxyl or -OP groups, wherein P represents a hydroxyl protecting group.

2. A compound in accordance with claim 1 wherein said C3–6 alkyl group is substituted with 2 hydroxyl groups and one -OP group wherein P is a hydroxyl protecting group.

3. A compound in accordance with claim 2 wherein P represents $CH_3C(O)$.

4. A compound in accordance with claim 1 wherein $R^1$ represents a branched $C_{5-15}$ alkyl group.

5. A compound in accordance with claim 3 wherein $R^1$ represents a $C_{10}$ branched alkyl group.

6. A compound in accordance with claim 5 of the formula:

7. A compound in accordance with claim 1 having the structural formula:

-continued or

8. A pharmaceutical composition which is comprised of a compound in accordance with claim 1 in combination with a pharmaceutically acceptable carrier.

9. A method of treating a fungal infection in a mammal in need of such treatment, comprising administering to said mammal a compound in accordance with claim 1 in an amount effective to treat a fungal infection.

* * * * *

UNITED STATES PATENT AND TRADEMARK OFFICE
CERTIFICATE OF CORRECTION

PATENT NO. : 5,543,431
DATED : August 6, 1996
INVENTOR(S) : E. A. Bolessa, et al.

It is certified that error appears in the above-identified patent and that said Letters Patent is hereby corrected as shown below:

Column 5, line 36 should read as follows:

- - strain, Merck number MF5866 (ATCC 74288) in a solid - -.

Signed and Sealed this

Fifteenth Day of September, 1998

Attest:

BRUCE LEHMAN

Attesting Officer

Commissioner of Patents and Trademarks